United States Patent [19]

Leigh

[11] 3,981,996
[45] Sept. 21, 1976

[54] PHARMACEUTICAL SKIN COMPOSITIONS

[75] Inventor: Steven Leigh, South Croydon, England

[73] Assignee: Vymatt S.A., Lugano, Switzerland

[22] Filed: June 20, 1974

[21] Appl. No.: 481,449

Related U.S. Application Data

[63] Continuation-in-part of Ser. No. 334,274, Feb. 21, 1973, abandoned.

[52] U.S. Cl. ................................. 424/243; 424/94; 424/115; 424/227; 424/230; 424/237; 424/242; 424/271; 424/285; 424/320; 424/322; 424/337; 424/346; 424/357; 424/361; 424/365

[51] Int. Cl.$^2$ ................ A61K 31/56; A61K 37/48; A61K 47/00

[58] Field of Search ........... 424/365, 357, 322, 361, 424/337, 320, 285, 242, 230, 237, 271, 94, 115, 346, 243, 227

[56] References Cited

UNITED STATES PATENTS

| | | | |
|---|---|---|---|
| 2,346,632 | 4/1944 | Wolfert et al. | 424/322 |
| 2,665,256 | 1/1954 | Barker | 424/322 |
| 3,666,863 | 5/1972 | Swanbeck | 424/322 |

*Primary Examiner*—Sam Rosen
*Attorney, Agent, or Firm*—Wenderoth, Lind & Ponack

[57] ABSTRACT

A novel drug delivery system in the form of a skin cream comprises a continuous hydrophobic medium in which there is dispersed an inert water-insoluble powder, the particles of which carry absorbed thereon an aqueous solution or dispersion of a medicament. Improved percutaneous transportation of medicaments by the system is claimed.

11 Claims, 1 Drawing Figure

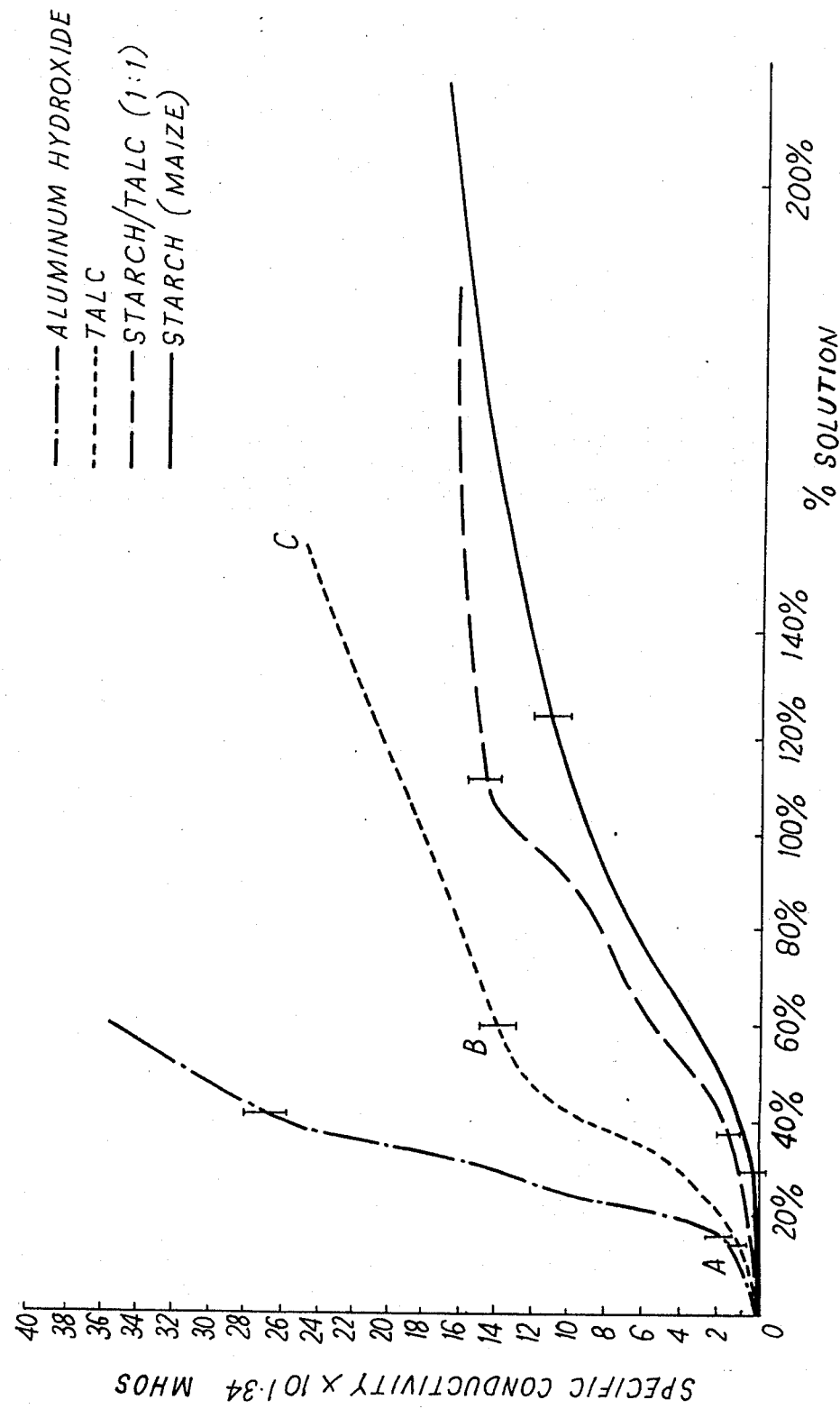

PHARMACEUTICAL SKIN COMPOSITIONS

This application is a continuation-in-part of application Ser. No. 334274 filed Feb. 21, 1973, now abandoned.

This invention relates to pharmaceutical compositions, suitable for external application to human skin, comprising a continuous hydrophobic phase in which there is dispersed an inert water-insoluble powder the particles of which carry adsorbed thereon an aqueous solution or dispersion of a medicament.

The hydrophobic phase may be present as a liquid, semi-solid, gel or solid medium; the nature is not critical to this invention, and may consist of any hydrophobic material conventionally used in pharmaceutical compositions. These include oils of vegetable and mineral origin such as liquid paraffin, and white soft paraffin, silicone oil and isopropyl myristate. Thickeners, for example silica compounds, beeswax and microcrystalline wax may be used as desired. Our preferred hydrophobic medium is white soft paraffin.

The water-insoluble powder is chosen to be inert to the hydrophobic medium and to the medicament, and may be one of the wide range of powders that is conventionally used in pharmaceutical preparations, for example:
1. polysaccharides such as starch and ethyl cellulose;
2. silica and inorganic silicates such as talc, kaolin, attapulgite and diatomites;
3. synthetic plastics polymers such as acrylic, vinyl and phenolic resins;
4. inorganic materials such as aluminum hydroxide, magnesium hydroxide and calcium phosphate.

It is preferred that the average particle size of the powder should be from 1 micron to 30 microns. While this range is not critical, powders above 30 microns tend to impart a coarse texture to pharmaceutical compositions, while powders in the sub-micron range are approaching colloidal size and are liable to affect the physical properties of the medium. Thus, for example, colloidal silica may be used as a thickener for the hydrophobic medium, while a coarser grade of silica could be used (though it is not preferred) as the powder on which the aqueous solution is adsorbed.

In one important aspect, the compositions of this invention provide a novel drug delivery system for the presentation of medicaments intended for application to the skin.

The system has a number of advantages over conventional systems. Thus, it enables medicaments to be used in concentrated aqueous solution or dispersion, in which form they are generally most effective, without the problems of irritancy that are often associated with concentrated solutions; in this context, the inert powder and the hydrophobic medium are acting as diluents. The inert powder mitigates the greasy texture of the hydrophobic medium. It has also surprisingly been found that aqueous solutions and dispersions of medicaments which are normally rather unstable show improved stability when adsorbed on a powder and presented as a composition according to this invention. Thus, while the nature of the medicament is not critical, the invention is of particular advantage in relation to medicaments which are prone to hydrolysis or oxidation in the presence of water. Examples are proteolytic and mucolytic enzymes and antibiotics and a group of polar organic compounds consisting of urea, dimethyylsulphoxide (DMSO), dimethylacetamide (DMA), dimethylformamide (DMF), and tetrahydrofurfuryl alcohol (THFA).

Suitable enzymes include acetylcysteine (10% to 20% by weight of the composition); the bromelaines (25000 to 100000 I.U. per gram); and hyaluronidase (0.1% to 1% by weight of the composition). Suitable antibiotics include the tetracyclines and the penicillins (typically from 0.01% to 2% by weight of the composition).

Other examples will readily occur to those skilled in the art of formulating pharmaceutical composition.

Urea is well known as an agent for the treatment of hyperkeratotic conditions of the skin. In addition to being of therapeutic value of itself, urea can also act as a hydrating agent by becoming bound to water molecules. In particular, it is capable of hydrating the skin so as to allow the percutaneous transportation of medication, thus acting as a drug delivery system. The use of urea in the treatment of skin conditions is, however, severely restricted by the fact that urea is unstable in neutral aqueous solution and tends to decompose with th liberation of carbon dioxide and ammonia. This difficulty has never really been overcome, with the result that urea has never achieved widespread use in compositions for skin treatment. An indication of the difficulty is given by the fact that one skin cream on the market contains urea buffered at a pH of about 2.0; of course the very high acid level of this cream causes it to sting on application, and makes it quite unsuitable for use in many instances.

By contrast, urea, in an aqueous solution which is adsorbed on to particles of an inert powder, is sufficiently stable to be formulated into skin cream and other pharmaceutical preparations. The aqueous solution may be buffered to a particular pH, but buffering is not essential to maintain the stability of the urea. The pH of pharmaceutical compositions according to this invention is therefore not critical, though it will normally be from 4 to 9 for the comfort of the patient.

When urea or other polar organic compound is present in aqueous solution adsorbed on the particles of inert powder, the pharmaceutical compositions of this invention may advantageously contain one or more other medicament. Moreover, the fact that the percutaneous transportation of these other medicaments is assisted by the urea or other polar organic compounds means that often less medicament can be used with a consequent saving in costs and other advantages. Such medicaments will often be present in the hydrophobic, rather than the hydrophilic, phase of the composition. The nature of such medicaments is not critical to the invention, those which are conventional for topical application may be used, for example:

a. Corticosteroids and derivatives thereof, for example hydrocortisone and the fluorinated corticosteroids, generally in a proportion of from 0.01% to 2% by weight on the weight of the composition. One advantage of the presence of urea or other polar organic compound is that smaller quantities of other medicaments can be used to achieve the same effect. This advantage may be crucial in the particular case of fluorinated corticosteroids, whose use is fraught with undesirable side-effects, and discontinuance of which can give rise to a rebound effect. In particular, it may be possible to provide compositions according to this invention in which less than 0.1% by weight of a fluorinated corticosteroid provides a useful therapeutic effect.

b. Dithranol, which is used for the treatment of the very common non-malignant form of skin cancer called psoriasis, generally in amounts from 0.01% to 2% by weight on the weight of the composition. Dithranol is very corrosive and stains the skin, and therefore needs to be used in low concentration. In compositions according to this invention, useful therapeutic effects may be obtained with less than 0.1% by weight of dithranol.

c. Salicylates for the treatment of rheumatic conditions, generally in an amount from 0.25% to 10% by weight on the weight of the composition. An example of such a salicylate is that sold by the Sterling-Winthrop Group under the Trade Name Benorylate.

d. Griseofulvin and related antifungal agents, generally in an amount of from 0.1% to 3% by weight on the weight of the composition. Griseofulvin is poorly absorbed through the skin, and the treatment of conditions such as ringworm and athletes foot has generally involved oral as well as topical administration. The improved percutaneous absorption of medicaments from compositions containing urea or another polar organic compound (DMSO is particularly suitable) of this invention may enable the oral administration of griseofulvin to be dispensed with.

e. Sun screening preparations comprising mixtures of vitamins A and D, generally in an amount of from 50,000 to 5,000,000 i.u. per gram.

The hydrophobic phase normally needs to be present in a greater amount than the aqueous solution, in order that the hydrophobic phase is continuous, and preferably constitutes from 20% to 80%, particularly from 20% to 50%, by weight on the weight of the composition.

The inert powder is preferably present in an amount of from 5% to 60% by weight on the weight of the composition. The preferred powders (e.g. starch, inorganic silicates, talc) may advantageously be used in amounts from 25% to 50%. Alternative powders (e.g. diatomites, aluminium hydroxide and magnesium hydroxide) should preferably be below 20%.

The aqueous solution present is largely determined by the proportion of the other ingredients. The aqueous medium should not normally predominate over the hydrophobic medium since it is desired that the latter should be continuous. There should not normally be very much more aqueous medium than powder, since it is desired that the aqueous medium be adsorbed on the particles of the powder. Subject to these provisos, the aqueous medium is preferably present in an amount of from 5% to 40%, particularly 10% to 25%, by weight on the weight of the composition. The proportion of solute (e.g. urea and/or other medicament) in the aqueous medium will generally be as high as possible, on the basis that concentrated solutions are somewhat less prone to decomposition than dilute ones. Urea, for example, dissolves in its own weight of water, and is generally used in near saturated solution. The proportion of urea or other polar compound (when used) in the composition is preferably 1% to 20%, particularly 5% to 15%, by weight. The solvent of the aqueous medium is preferably at least predominantly water, but may contain a minor or even a major proportion of one or more hydrophilic organic liquids, for example, ethyl alcohol, propylene glycol or glycerol.

Other ingredients may be present in the compositions of this invention such as are conventionally present in water-in-oil emulsion pharmaceutical formulations, for example, antioxidants, bacteriostats, buffers, surfaceactive agents, thickeners, colouring matter and perfume. Fatty acid esters may be present, generally in amounts up to 10% by weight. Humectants, for example, propylene glycol and sorbitol, may be present, generally in amounts up to 5% by weight.

The pharmaceutical compositions of this invention can be prepared by simply mixing the various ingredients in any convenient order. Thus, for example:- a. the aqueous solution may be added to the powder so as to be adsorbed on the surface of the particles, and the resulting material, which will be freeflowing if only a relatively small amount of liquid has been used, mixed into the hydrophobic base, if necessary at an elevated temperature;

b. the inert powder may be mixed into the hydrophobic base and the aqueous solution added gradually to the mixture, when it will become adsorbed on the particles of powder;

c. the aqueous solution may be mixed with the hydrophobic base so as to form a water-in-oil emulsion to which the inert powder is gradually added.

The amount of liquid that is advantageously adsorbed on the particles of the inert powder depends to a substantial extent on the properties of the powder, and can be conveniently checked by measuring the electrical conductivity of the powder/aqueous solution mixture. This is illustrated in the accompanying drawing, which is a graph of the specific conductivities of four powders to which different amounts (expressed in % by weight on the weight of the dry powder) of an aqueous solution of urea (specific conductivity 90 $\mu$ mhos) have been added.

Each curve shows a first region, commencing at the origin O, where the extent of adsorption is incomplete and the specific conductivity is low. Each curve is sigmoidal, with a mid-region which may be regarded as optimum adsorption. Where the amount of aqueous solvent is excessive, particularly where the quantity of solvent exceeds the quantity of powder, a slurry-suspension results, wherein the solvent is not bound to the powder particle surface as an adsorbed layer but carries the powder in suspension or as a slurry. In this region, the curve becomes asymptotic. The mid-region of optimum adsorption is bounded substantially by the two, opposite, inflexions of the curve concerned, lettered A and B.

It may be noted that, of the four powder matrixes exemplified, the polysaccharide (starch) powder has the highest capacity to adsorb the aqueous solvent and the metallic hydroxide (aluminium hydroxide) powder has the lowest capacity.

Pharmaceutical compositions according to the invention are prepared in the manner of a water-in-oil type emulsion. Hence, they might be expected to be consistent with water-in-oil type emulsions generally and to be electrically non-conductive.

Surprisingly, however, in the method of dispersing the powder particles, with adsorbed electrolyte aqueous solution, in a hydrophobic base, a transition occurs at which the emulsion becomes electrically conductive.

If spaced-apart electrodes are placed in the hydrophobic component while the powder with adsorbed electrolyte is added, a point is reached beyond which electricity will flow between the electrodes.

The effect is as though the electrolyte solution on the discrete powder particles forms a continuous electrolyte bridge between the electrodes. This conductivity transition can be taken generally as denoting one satisfactory composition, both in respect of the quality of electrolyte solution adsorbed on to the inert powder and in respect of the quantity of powder, with adsorbed electrolyte, added to the hydrophobic component.

Thus, for example, an aqueous solution of urea has a specific conductivity of 90 $\mu$ mhos. An inert powder, starch, is practically non-conductive, having a specific conductivity of 0.10 $\mu$ mho. The hydrophobic component, white soft paraffin, is effectively an electrical insulator. The measured specific conductivity is 0.15 $\mu$ mho, a value which is thought to reflect some inherent electrical leakage.

When a typical quantity of the urea solution is adsorbed on to the starch, the resultant intermediate component has a measured specific conductivity of 9.38 $\mu$ mhos.

As the powder bearing adsorbed urea solution is added to the hydrophobic component, the measured specific conductivity is initially 0.15 $\mu$ mho and remains at this figure until, when a typical quantity of powder is added to form a powder cream according to the invention, the measured specific conductivity changes from 0.15 $\mu$ mho to 1.35 $\mu$ mhos, denoting a different order of conductivity.

By way of comparison, a dispersion of dry powder in the hydrophobic medium gives the same specific conductivity of 0.15 $\mu$ mho. Similarly, a dispersion of urea solution in the hydrophobic medium gives the same specific conductivity of 0.15 $\mu$ mho.

The conductivity measurements for the two comparison systems support the belief that a cream according to the invention with electrolyte solution adsorbed on a powder matrix dispersed in a wax or oil component might be expected to be electically non-conductive.

The measured conductivity transition, however, showing a specific conductivity of 1.35 $\mu$ mhos, is evidence of a surprising dissimilarity of conductivity characteristic for a powder cream according to the invention.

Thus, it can be said that pharmaceutical compositions according to the invention have a specific electrical conductivity of at least 0.5 $\mu$ mho. and preferably of at least 1.0 $\mu$ mho.

The following Examples illustrate the invention.

EXAMPLE 1

| | |
|---|---|
| urea | 10 g |
| water | 10 g |
| starch | 30 g |
| white soft paraffin to | 100 g |

The urea is completely dissolved in 10 g of water at room temperature to form a solution with a specific conductivity of 90 $\mu$ mho. This solution is adsorbed on to the starch matrix resulting in an adsorbed system with a conductivity of 9 $\mu$ mho. The uniform dispersion of the adsorbed material in the white paraffin base gives rise to a powder-cream with a conductivity of approximately 1 $\mu$ mho.

EXAMPLE 2

| | |
|---|---|
| urea | 10 g |
| water | 10 g |
| starch | 30 g |
| oleyl alcohol | 5 g |
| white soft paraffin to | 100 g |

It has been found that the physical appearance of the final product may be improved if a modifying oil, such as oleyl alcohol, is included. The oleyl alcohol is added in the final stage of the preparation of the composition,

EXAMPLE 3

It has furthermore been found that the base may be rendered more hydrophilic if a surface-active agent with an H.L.B. value between 9 to 14 is include. A specific example of such a surface-active agent is polyoxyethylene nonyl ether with an H.L.B. value of about 11.

| | |
|---|---|
| urea | 10 g |
| water | 10 g |
| starch | 30 g |
| polyoxyethylene nonyl ether | 1 g |
| oleyl alcohol | 5 g |
| white soft paraffin to | 100 g |

In this example, according to the method of the invention described above, the urea is first dissolved in the water and is then adsorbed on to the starch, in this example with the polyoxyethylene nonyl ether. The powder with adsorbed aqueous solution is then dispersed in the white soft paraffin base to provide the final powder cream.

In this example, according to an alternative method according to the invention, the starch powder is first dispersed in the white soft paraffin base, so providing an intermediate dispersion. The aqueous solution is then added slowly to the intermediate composition and, with suitable agitation, becomes adsorbed on to the dispersed powder particles.

In this example, according to yet another alternative method according to the invention, the aqueous solution is first added to the white soft paraffin base, so providing an intermediate, water-in-oil type emulsion. The starch powder is then added slowly to the intermediate emulsion and, with suitable agitation adsorbs the aqueous solution on to the particle surfaces.

EXAMPLE 4

To improve the chemical stability of the composition, it is often desirable to dissolve the urea in a solution of water and a non-aqueous solvent. Accordingly, in this example propylene glycol has been used to replace some of the water.

| | |
|---|---|
| urea | 10 g |
| water | 8 g |
| propylene glycol | 5 g |
| starch | 35 g |
| polyoxyethylene nonyl ether | 2 g |
| oleyl alcohol | 4 g |
| white soft paraffin to | 100 g |

The urea is dissolved in the water/propylene glycol mixture without the aid of heat.

EXAMPLE 5

| | | |
|---|---|---|
| urea | 10 g | |
| water | 7.5 g | A |
| ethyl alcohol | 10 g | |
| starch | 25 g | B |
| polyoxyethylene nonyl ether | 2 g | |
| oleyl alcohol | 4 g | C |
| white soft paraffin to | 100 g | |

The urea is dissolved in the water/alcohol mixture to form intermediate composition A. A is then adsorbed on to B, and allowed to dry at room temperature until a free-flowing intermediate powder is obtained. This is admixed evenly into C to give a urea powder-cream.

EXAMPLE 6

| | |
|---|---|
| urea | 10 g |
| water | 14 g |
| dry starch | 27 g |
| white soft paraffin | 26 g |
| sorbitol | 1 g |
| polyoxyethylene fatty ester | 9 g |
| sorbitan monolaurate | 2 g |
| isopropyl myristrate | 10 g |
| hydrocortisone and/or fluorinated corticosteroids | 1 g |

The specific electrical conductivity of the formulation is 1.35 $\mu$ mhos.

The urea in the formulation can be replaced by the same weight of dimethylsulphoxide, dimethylformamide, dimethylacetamide or tetrahydrofurfuryl alcohol.

In the above formulation, there can be used, instead of or as well as the corticosteroid:-
a. 0.1 g of dithranol;
b. 2 g of para-N-acetylaminophenyl acetylsalicylate;
c. 1 g og griseofulvin; or
d. 50 million i.u. of a mixture of vitamins A and D.

It is often desirable to use a combination or blend of starch and other inert base powder in any suitable ratio and therefore, in Example 6, in place of 27% dry starch, suitable alternative powder compositions are: starch and inorganic silicate in the ratio of 1:1, 2:1, 3:1;

starch and synthetic plastic polymers in the ratio of 1:1, 2:1, 3:1, 4:1;

starch and aluminium hydroxide, magnesium hydroxide, clacium phosphate in the ratio of 3:1, 4:1, 5:1;
starch and diatomites in the ratio of 4:1, 5:1, 6:1;
(any one of these combinations should comprise 27% of the final weight of the composition). In any case, the conductivity of the powder matrix with the adsorbed solution should preferably fall within the mid-region of the curve corresponding to those of the drawing.

I claim:

1. A pharmaceutical composition, suitable for external application to human skin, which composition comprises a continuous hydrophobic phase of a pharmaceutically acceptable liquid, semi-solid, gel or solid material, having dispersed therein a pharmaceutically acceptable water-insoluble powder the particles of which carry adsorbed thereon an aqueous solution or dispersion of a member selected from the group consisting of (a) a polar organic compound selected from urea, dimethylsulphoxide, dimethylacetamide, dimeltylformamide, and tetrahydrofurfuryl alcohol, (b) a medicament and (c) mixtures of (a) and (b), said water-insoluble powder being inert to the hydrophobic medium and to the medicament and having an average particle size of greater than about 1 micron, and wherein the proportion of hydrophobic phase is from 20% to 80% by weight of the composition, the proportion of inert powder is from 5% to 60 % by weight of the composition, and the proportion of aqueous solution or dispersion is from 5% to 40% by weight of the composition.

2. A composition as claimed in claim 1, wherein the hydrophobic phase comprises white soft paraffin.

3. A composition as claimed in claim 1, wherein the inert water-insoluble powder comprises starch.

4. A composition as claimed in claim 1, wherein the average size of the powder is from 1 micron to 30 microns.

5. A composition as claimed in claim 1, wherein:- the proportion of hydrophobic medium is from 20% to 50% by weight;
the proportion of inert powder is from 25% to 50% by weight;
the proportion of aqueous solution or dispersion is from 10% to 25% by weight;
provided that the proportion of water does not exceed the proportion of hydrophobic phase.

6. A composition as claimed in claim 1, wherein the medicament is selected from proteolytic and mucolytic enzymes and antibiotics.

7. A composition as claimed in claim 1, wherein the specific conductivity of the inert powder/aqueous solution or dispersion component lies on the sigmoidal portion of a graph of specific electrical conductivity against amounts of aqueous solution or dispersion adsorbed on the powder.

8. A composition as claimed in claim 1, having a specific electrical conductivity of at least 0.5 $\mu$ mho.

9. A composition as claimed in claim 1, containing in percent by weight:-

| | |
|---|---|
| Urea | 10% |
| water | 14% |
| Dry starch (polysaccharide) | 27% |
| White soft paraffin | 26% |
| Sorbitol | 1% |
| Polyoxyethylene fatty ester | 9% |
| Sorbitan monolaurate | 2% |
| Isopropyl myristate | 10% |
| Hydrocortisone and/or a fluorinated cortico-steroid | 1%. |

10. A composition as claimed in claim 1 wherein the polar organic compound is present in an amount of from 5% to 15% by weight of the composition.

11. A composition as in claim 10 wherein there is also present at least one member of the group of corticosteroids dithranol, salicylates, griseofulvin, and mixtures of Vitamins A and D.

* * * * *